_United States Patent_ [19]

Gognaco

[11] 3,941,833

[45] Mar. 2, 1976

[54] AMINO DERIVATIVES OF 2,2-DIARYL-CYCLOPROPANE

[75] Inventor: Jean-Claude Gognaco, Garches, France

[73] Assignee: Societe Anonyme dite: HEXACHIMIE, France

[22] Filed: Nov. 19, 1973

[21] Appl. No.: 417,128

[30] Foreign Application Priority Data
Nov. 30, 1972 United Kingdom............... 55277/72

[52] U.S. Cl.......... 260/472; 260/473 R; 260/558 R; 260/559 P; 260/567 CM; 260/570.5 CA; 260/570.8 C; 260/477; 260/308; 260/324; 260/330
[51] Int. Cl.².......................................... C07C 93/24
[58] Field of Search............ 260/471 R, 473 R, 477, 260/570.6, 472

[56] References Cited
OTHER PUBLICATIONS
Finar, I. L.; *Organic Chemistry*, Vol. I, (1963), pub. by Richard Clay & Co., Great Britain, pp. 193, 205 & 292 cited.
Klosa, J.; Prakt. Chem. 35, 133 (1967).

*Primary Examiner*—Robert Gerstl
*Attorney, Agent, or Firm*—Bacon & Thomas

[57] ABSTRACT

The present invention relates to compounds of the general formula

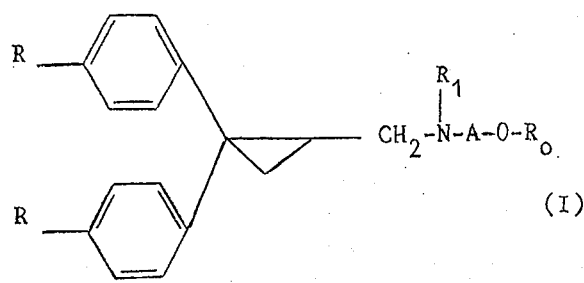

(I)

in which R represents the hydrogen atom, a halogen atom, a lower alkyl group or a lower alkoxy group; $R_1$ represents the hydrogen atom, a lower alkyl group, preferably methyl, or an aralkyl group; A represents an alkylene group; and $R_0$ represents the hydrogen atom or an acyl group; and their acid addition salts as new industrial products.

These new products are suitable for use in the treatment of cardiac disorders.

9 Claims, No Drawings

AMINO DERIVATIVES OF 2,2-DIARYL-CYCLOPROPANE

This invention relates to new amine derivatives of 2,2-diaryl cyclopropane as new industrial products. The invention also relates to processes for their preparation, to their therapeutic application and to the new intermediate products from which they can be synthesised.

More particularly, the invention relates to amino alcohol compounds of 2,2-diaryl cyclopropane and to the amino ester derivatives resulting from them.

Accordingly, it is an object of the present invention to provide novel compounds selected from the group consisting of:

a. amine derivatives of 2,2-diaryl cyclopropane corresponding to the general formula

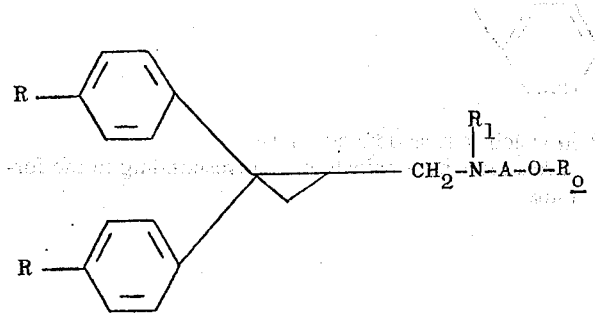

(I)

in which
R represents the hydrogen atom, a halogen atom, a lower alkyl group or a lower alkoxy group;
$R_1$ represents the hydrogen atom, a lower alkyl group, preferably methyl, or an aralkyl group;
A represents an alkylene group; and
$R_o$ represents the hydrogen atom or an acyl group;

and
b. their acid addition salts.

In the context of the invention, lower alkyl and alkoxy groups are groups containing from 1 to 5 carbon atoms. The preferred halogen atoms R are the fluorine, chlorine and bromine atoms. The alkylene group A is preferably a linear or branched divalent hydrocarbon chain containing 1 to 5 carbon atoms.

Among the acyl grups $R_o$, the preferred group is a benzoyl group whose aromatic nucleus can be substituted. More particularly, the benzoyl group $R_o$ corresponds to the formula

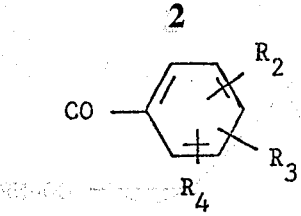

in which $R_2$, $R_3$ and $R_4$, which can be the same or different, each represent the hydrogen atom, a lower alkyl group, a lower alkoxy group, a halogen atom or the nitro group.

To prepare the compounds of formula I in which $R_o$ is an acyl group, a compound of formula I in which $R_o$ represents hydrogen is esterified by a method known per se; this compound can be synthesised either from an alkyl 2,2-diaryl cyclopropane carboxylate (method A) or from a 1-cyano-2,2-diaryl cyclopropane (method B).

To prepare a compound of formula I in which $R_o$ represents hydrogen by method A, a. an ester of 2,2-diaryl cyclopropane carboxylic acid corresponding to the formula

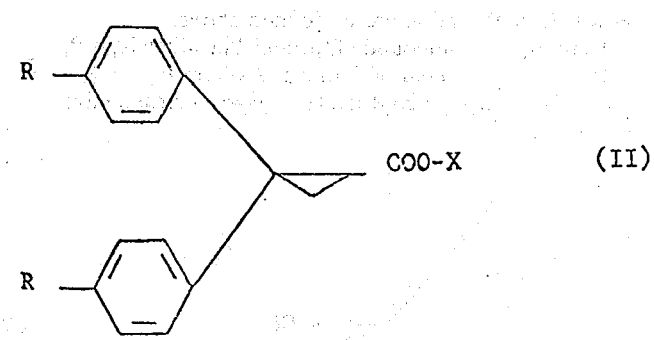

(II)

in which R is as defined above and X represents a lower alkyl group, preferably ethyl, is reacted with an amino alcohol corresponding to the formula $$HN(R_1) - A - OH \qquad (III)$$

in which $R_1$ and A are as defined above, and
b. the hydroxyamide thus obtained which corresponds to the formula

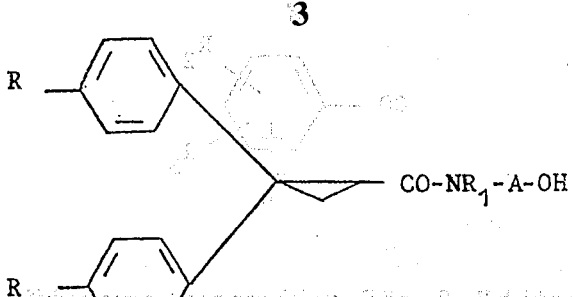

in which R, $R_1$ and A are as defined above,
is reduced with $LiAlH_4$ in an inert anhydrous solvent to form a compound corresponding to the formula

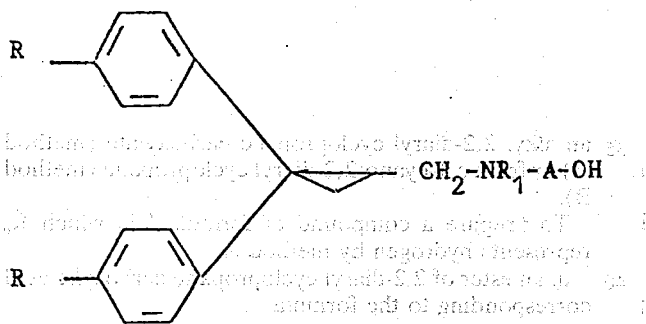

in which R, $R_1$ and A are as defined above.

To prepare a compound of formula I in which $R_1 = R_o$ = H (i.e. a compound of formula V where $R_1$ = H), a. a 1-cyano-2,2-diaryl cyclopropane corresponding to the formula

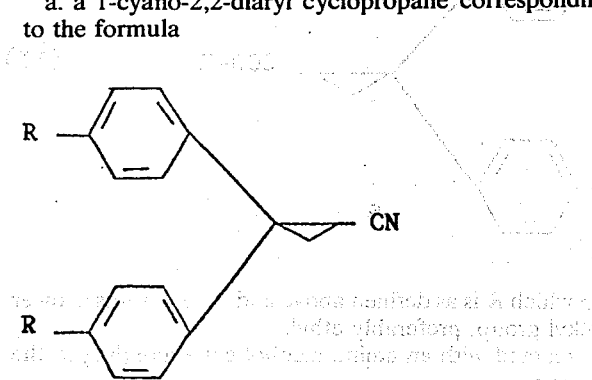

in which R is as defined above,
is catalytically reduced with Raney nickel under a pressure of 40 to 60 atmospheres at a temperature of around 80°C in an alcohol/ammonia medium, the alcohol being methanol or ethanol, and b. the amine thus obtained which corresponds to the formula

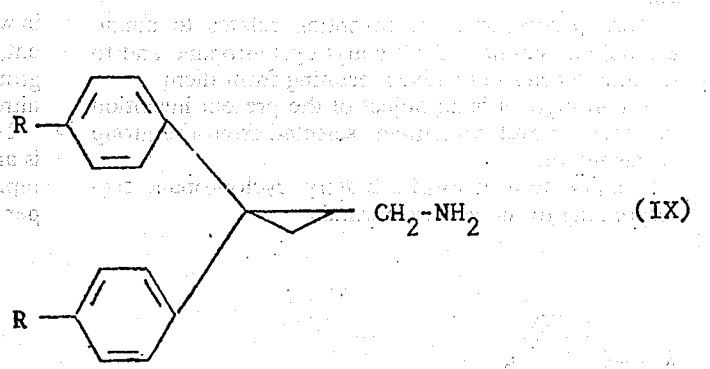

in which R is as defined above,
is reacted with a haloalcohol corresponding to the formula $$Y - A - OH \qquad (X)$$

in which Y is chlorine, bromine or iodine and A is as defined above,
to form a compound of formula V in which $R_1$ represents hydrogen.

To obtain compounds of formula I in which $R_o$ is acyl, a product of formula V obtained by method A or method B is subjected to esterification. More particularly, an amino alcohol V can be reacted in the form of its hydrochloride with an acid chloride corresponding to the formula Cl — R₀ (VI)

in which R₀ represents an acyl group and, preferably, a benzoyl group of the formula

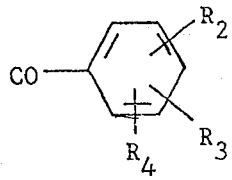

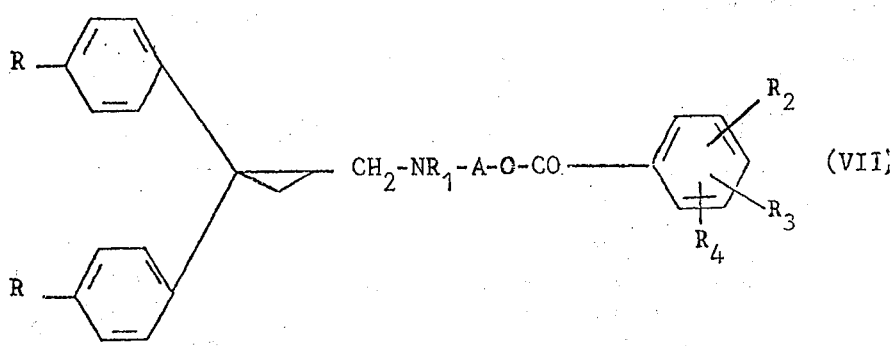

in which R₂, R₃ and R₄ are as defined above.

In one embodiment of method A, the reaction of an ester of formula II with an amino alcohol of formula III is carried out in an excess of the amino alcohol at the reflux temperature of this compound. The condensation of II and III can also be carried out in an inert solvent at the reflux temperature of that solvent.

The reduction of amide IV with LiAlH₄ is carried out in an inert non-aqueous solvent. The mixture of the reactants and solvent is prepared while cooling the reaction medium; the solvent is then heated to reflux temperature over a period of about 2 hours, the preferred solvent for this operation being tetrahydrofuran.

So far as method B is concerned, the reduction stage (a) is preferably carried out in an NH₃/lower alcohol (ethanol or methanol) medium containing 100 g of NH₃ per liter of alcohol. The reaction stage (b) is carried out in an aromatic solvent, especially toluene, xylene and mixtures thereof, at the reflux temperature of that solvent over a period of at least 1 hour and, preferably, over a period of 7 hours.

To prepare an acyl derivative of formula I, the hydrochloride of a compound of formula V is reacted with an acid chloride Cl—R₀ in stoichiometric proportions or in the presence of a slight excess of acid chloride in an anhydrous solvent at the reflux temperature of this solvent. The solvent preferably used for this reaction is chloroform.

The compounds of formula I, IV, V and IX can be converted into the corresponding acid addition salts by reaction with a mineral or organic acid. Acids particularly suitable for this purpose include hydrochloric acid, sulphuric acid, acids of phosphorus, oxalic acid, succinic acid, methane sulphonic acid, cyclohexyl sulphamic acid, formic acid, aspartic acid, glutamic acid, N-acetyl aspartic acid, N-acetyl glutamic acid, ascorbic acid, maleic acid, malic acid, fumaric acid, lactic acid, benzoic acid and cinnamic acid.

The new intermediate compounds according to the invention are ethyl 2,2-diparafluorophenyl cyclopropane carboxylate, the hydroxyamides of formula IV and the amines of formula IX.

For therapeutic applications, at least one compound of formula I or one of its non-toxic acid addition salts is used in association with a physiologically acceptable excipient in therapeutic compositions suitable in particular for the treatment of disorders affecting the cardiovascular system.

In one preferred embodiment, recommended therapeutic compositions are those which contain at least one acyl compound corresponding to the formula in which R, R₁, R₂, R₃, R₄ and A are as defined above, or one of its non-toxic acid addition salts as active ingredient.

Other advantages and features of the invention will be better understood on reading the following description of examples of preparation which are purely illustrative and by no means limitative.

In the following, Examples 1 to 14 relate to the preparation of compounds of formula V and their intermediates by method A, Examples 25 to 30 relate to the preparation of compounds of formula V and their intermediates by method B whilst Examples 15 to 24 relate to the preparation of compounds of formula I in which R₀ is acyl (the developed formulae of these latter products are given in the following).

EXAMPLE 1

Ethyl 2,2-di-p-fluorophenyl cyclopropane carboxylate (Formula II R = F)

0.44 Mole of ethylacrylate are added dropwise with stirring to 0.4 mole of di-p-fluorophenyl diazomethane in 300 cc of chloroform, the temperature being kept at around 40°C if necessary with a cold water bath.

On completion of the addition, the mixture is stirred.

After 5 hours, the solution is colourless and the evolution of nitrogen at an end.

The solvent is evaporated in vacuo and the oil thus obtained is used as such for the remaining operations. Yield: 92 %

The ethyl ester thus prepared is characterised by the corresponding acid obtained after boiling for 2 hours in methanol in the presence of 2 equivalents of KOH.

| | |
|---|---|
| Yield of acid: | 80 % |
| Melting point of the acid: | 130°C |
| Analysis: | |

-continued

| Calculated | Found |
|---|---|
| C : 70.1 % | C : 70.24 % |
| H : 4.37 % | H : 4.21 % |

EXAMPLE 2

N-β-Hydroxyethyl-2,2-diphenyl cyclopropane carboxamide (Formula IV R = $R_1$ = H, A = $CH_2CH_2$)

0.1 Mole of ethyl 2,2-diphenyl cyclopropane carboxylate and 0.15 mole of ethanolamine are heated to reflux and the ethanol formed distilled off. The reaction is over after 5 hours. The reaction product is cooled and crystallised in a mixture of ether and petroleum ether (60 : 40).

| Yield: | 71 % |
|---|---|
| Melting point: | 109°C |
| Analysis: | |
| Calculated | Found |
| N : 4.98 % | N : 4.83 % |

EXAMPLE 3

N-γ-Hydroxypropyl-2,2-diphenyl cyclopropane carboxamide (Formula IV R = $R_1$ = H, A = $(CH_2)_3$ The procedure is as in Example 2, except that the ethanolamine is replaced by an equivalent quantity of γ-propanolamine (0.15 mole).

| Yield: | 67 % |
|---|---|
| Melting point: | 92°C |
| Analysis: | |
| Calculated | Found |
| N 4.75 % | N 4.60 % |

EXAMPLE 4

N-β-Hydroxyethyl-N-methyl-2,2-diphenyl cyclopropane carboxamide (Formula IV R = H, $R_1$ = $CH_3$, A = $CH_2CH_2$)

The procedure is as in Example 2 except that the ethanolamine is replaced by an equivalent quantity of N-methyl ethanolamine. After cooling, the reaction mixture is taken up with dilute hydrochloric acid, extracted with ether, dried over magnesium sulphate and the ether removed in vacuo, leaving an oil which is used as such for the remaining operations.

| Yield: | 78 % |
|---|---|
| Analysis: | |
| Calculated | Found |
| N 4.75% | N 4.40 % |

EXAMPLE 5

N-γ-Hydroxypropyl-2,2-di-p-tolyl cyclopropane carboxamide (Formula IV R = 4-$CH_3$, $R_1$ = H, A = $(CH_2)_3$)

The procedure is as in Example 4 using 0.1 mole of ethyl 2,2-di-p-tolyl cyclopropane carboxylate and 0.15 mole of γ-propanolamine. The oil thus obtained is used as such for the remaining operations.

| Yield: | 71 % |
|---|---|
| Analysis: | |
| Calculated | Found |
| N 4.33 % | N 3.96% |

EXAMPLE 6

N-γ-Hydroxypropyl-2,2-di-p-methoxyphenyl cyclopropane carboxamide (Formula IV R = 4-$OCH_3$, $R_1$ = H, A = $CH_2CH_2CH_2$)

The procedure is as in Example 4 using 0.1 mole of ethyl 2,2-di-p-methoxyphenyl cyclopropane carboxylate and 0.15 mole of γ-propanolamine. The resulting oil is used as such for the remaining operations.

| Yield: | 73 % |
|---|---|
| Analysis: | |
| Calculated | Found |
| N 3.94 % | N 3.77% |

EXAMPLE 7

N-γ-Hydroxypropyl-2,2-di-p-fluorophenyl cyclopropane carboxamide (Formula IV R = 4-F, $R_1$ = H, A = $CH_2CH_2CH_2$)

The procedure is as in Example 4 using 0.1 mole of ethyl 2,2-di-p-fluorophenyl cyclopropane carboxylate (prepared in accordance with Example 1) and 0.15 mole of γ-propanolamine. The oil obtained is used as such for the remaining operations.

| Yield: | 68% |
|---|---|
| Analysis: | |
| Calculated | Found |
| N 4.23% | N 3.96 % |

EXAMPLE 8

N-γ-Hydroxypropyl-2,2-di-p-chlorophenyl cyclopropane carboxamide (Formula IV R = 4-Cl, $R_1$ = H, A = $CH_2CH_2CH_2$)

The procedure is as in Example 4 using 0.1 mole of ethyl 2,2-di-p-chlorophenyl cyclopropane carboxylate and 0.15 mole of γ-propanolamine. The resulting oil is used as such for the remaining operations.

| Yield: | 69 % |
|---|---|
| Analysis: | |
| Calculated | Found |
| N 3.85 % | N 3.57 % |

EXAMPLE 9

1-(N-γ-Hydroxypropyl)-aminomethyl-2,2-diphenyl cyclopropane hydrochloride (Formula V R = $R_1$ = H, A = $CH_2CH_2CH_2$)

A solution of 0.1 mole of the amide of formula IV in 100 cc of anhydrous tetrahydrofuran, prepared in accordance with Example 3, is added dropwise while cooling to 0.15 mole of lithium tetrahydrogenoaluminate in 50 cc of anhydrous tetrahydrofuran. After the heat of reaction has abated, the reaction mixture is heated to reflux over a period of 2 hours, cooled, poured gradually onto ice, filtered, the insoluble component washed with ether, the filtrate collected and extracted with ether and the ether phase dried over magnesium sulphate.

Hydrogenchloride is added to the ethereal phase up to pH 1, the crystallised product is triturated, filtered, washed with ether and dried. The product is recrystallised from a mixture of isopropanol and ether (70 : 30).

| Yield: | 79 % |
|---|---|
| Melting point: | 178°C |
| Analysis: | |
| Calculated | Found |
| N 4.42 % | N 4.37 % |

EXAMPLE 10

1-(N-β-Hydroxyethyl)-aminomethyl-2,2-diphenyl cyclopropane hydrochloride (Formula V $R = R_1 = H$, $A = CH_2CH_2$)

The procedure is as in Example 9 using 0.1 mole of the amide of formula IV prepared in accordance with Example 2. The hydrochloride is recrystallised from a mixture of methanol and ether (80 : 20).

| Yield: | 81 % |
|---|---|
| Melting point: | 241 – 242°C |
| Analysis: | |
| Calculated | Found |
| N 4.62 % | N 4.69 % |

EXAMPLE 11

1-(N-β-Hydroxyethyl-N-methyl)-aminomethyl-2,2-diphenyl cyclopropane hydrochloride (Formula V $R = H$, $R_1 = CH_3$, $A = CH_2CH_2$)

The procedure is as in Example 9 using 0.1 mole of the amide of formula IV prepared in accordance with Example 4. The hydrochloride is recrystallised from a mixture of acetone and ether (70 : 30).

| Yield: | 72 % |
|---|---|
| Melting point: | 143°C |
| Analysis: | |
| Calculated | Found |
| N 4.41 % | N 4.40 % |

EXAMPLE 12

1-(N-γ-Hydroxypropyl)-aminomethyl-2,2-di-p-tolyl cyclopropane hydrochloride (Formula V $R = 4\text{-}CH_3$, $R_1 = H$, $A = CH_2CH_2CH_2$)

The procedure is as in Example 9 using 0.1 mole of the amide of formula IV prepared in accordance with Example 5. The hydrochloride is recrystallised from a mixture of isopropanol and ether (70 : 30).

| Yield: | 77 % |
|---|---|
| Melting point: | 195°C |
| Analysis: | |
| Calculated | Found |
| N 4.05 % | N 4.0 % |

EXAMPLE 13

1-(N-γ-Hydroxypropyl)-aminomethyl-2,2-di-p-methoxyphenyl cyclopropane hydrochloride (Formula V $R = 4\text{-}OCH_3$, $R_1 = H$, $A = CH_2CH_2CH_2$)

The procedure is as in Example 9 using 0.1 mole of the amide of formula IV prepared in accordance with Example 6. The hydrochloride is recrystallised from a mixture of isopropanol and ether (60 : 40).

| Yield: | 65 % |
|---|---|
| Melting point: | 131 – 132°C |
| Analysis: | |
| Calculated | Found |
| N 3.71 % | N 3.59 % |

EXAMPLE 14

1-(N-γ-Hydroxypropyl)-aminomethyl-2,2-di-p-fluorophenyl cyclopropane hydrochloride (Formula V $R = 4\text{-}F$, $R_1 = H$, $A = CH_2CH_2CH_2$)

The procedure is as in Example 9 using 0.1 mole of the amide of formula IV prepared in accordance with Example 7. The hydrochloride is recrystallised from a mixture of isopropanol and ether (70 : 30).

| Yield: | 69 % |
|---|---|
| Melting point: | 148 – 150°C |
| Analysis: | |
| Calculated | Found |
| N 3.96 % | N 3.87 % |

EXAMPLE 15

1-(N-γ-Hydroxypropyl)-aminomethyl-2,2-di-p-chlorophenyl cyclopropane hydrochloride (Formula V $R = 4\text{-}Cl$, $R_1 = H$, $A = CH_2CH_2CH_2$)

The procedure is as in Example 9 using 0.1 mole of the amide of formula IV prepared in accordance with Example 8. The hydrochloride is recrystallized from a mixture of ethanol and ether (80 : 20).

| Yield: | 50 % |
|---|---|
| Melting point: | 185°C |
| Analysis: | |
| Calculated | Found |
| N 3.62 % | N 3.45 % |

EXAMPLE 16

N-(2,2-Diphenyl cyclopropylmethyl)-γ-aminopropyl-3,4,5-trimethoxy benzoate hydrochloride (Formula VIIa)

0.055 Mole of 3,4,5-trimethoxy benzoyl chloride are added with stirring under reflux to a solution in 100 cc of anhydrous chloroform of 0.05 mole of 1-(N-γ-hydroxypropyl)aminomethyl-2,2-diphenyl cyclopropane hydrochloride prepared in accordance with Example 9. The mixture is kept under reflux for 6 hours, the solvent removed and the crude hydrochloride recrystallised from a mixture of ethanol and ether (80 : 20).

| Yield: | 65 % |
|---|---|
| Melting point: | 172°C |
| Analysis: | |
| Calculated | Found |
| N 2.74 % | N 2.90 % |

EXAMPLE 17

N-(2,2-Diphenyl cyclopropylmethyl)-γ-aminopropyl benzoate hydrochloride (Formula VIIb)

The procedure is an in Example 16 except that 0.055 mole of benzoyl chloride is used instead of 0.055 mole of 3,4,5-trimethoxy benzoyl chloride. The hydrochloride is recrystallised from a mixture of ethanol and ether (80 : 20).

| Yield: | 61 % |
|---|---|
| Melting point: | 188°C |
| Analysis: | |
| Calculated | Found |
| N 3.32 % | N 3.26 % |

EXAMPLE 18

N-(2,2-Diphenyl cyclopropylmethyl)-γ-aminopropyl-2-chlorobenzoate hydrochloride (Formula VIIc)

The procedure is as in Example 16 except that 0.055 mole of 2-chlorobenzoyl chloride is used instead of 0.055 mole of 3,4,5-trimethoxy benzoyl chloride. The hydrochloride is recrystallised from a mixture of ethanol and ether (80 : 20).

| Yield: | 67 % |
|---|---|
| Melting point: | 176°C |
| Analysis: | |
| Calculated | Found |
| N 3.07 % | N 3.0 % |

EXAMPLE 19

N-(2,2-Diphenyl cyclopropylmethyl)-γ-aminopropyl-3-nitrobenzoate hydrochloride (Formula VIId)

The procedure is as in Example 16 using 0.055 mole of 3-nitrobenzoyl chloride instead of 0.055 mole of 3,4,5-trimethoxybenzoyl chloride. The hydrochloride is recrystallised from a mixture of methanol and ether (80 : 20).

| Yield: | 70 % |
|---|---|
| Melting point: | 201 – 203°C |
| Analysis: | |
| Calculated | Found |
| N 6.0 % | N 5.84 % |

EXAMPLE 20

N-Methyl-N-[(2,2-diphenyl cyclopropyl)-methyl]-β-aminoethyl-3,4,5-trimethoxy benzoate hydrochloride (Formula VIIe)

Following the procedure of Example 16, 0.05 mole of 1-(N-β-hydroxyethyl-N-methyl)-aminomethyl-2,2-diphenyl cyclopropane hydrochloride, prepared in accordance with Example 11, are reacted with 0.055 mole of 3,4,5-trimethoxy benzoyl chloride. The hydrochloride is recrystallised from a mixture of isopropanol and ether (70 : 30).

| Yield: | 75 % |
|---|---|
| Melting point: | 156°C |
| Analysis: | |
| Calculated | Found |
| N 2.74 % | N 2.80 % |

EXAMPLE 21

N-[(2,2-Di-p-tolyl cyclopropyl)-methyl]-γ-aminopropyl-2-methyl benzoate hydrochloride (Formula VIIf)

Following the procedure of Example 16, 0.05 mole of 1-(N-γ-hydroxypropyl)-aminomethyl-2,2-di-p-tolyl cyclopropane hydrochloride, prepared in accordance with Example 11, are reacted with 0.055 mole of 2-methyl benzoyl chloride. The hydrochloride is recrystallised from a mixture of ethanol and ether (70 : 30).

| Yield: | 70 % |
|---|---|
| Melting point: | 181 – 183°C |
| Analysis: | |
| Calculated | Found |
| N 3.02 % | N 3.17 % |

EXAMPLE 22

N-](2,2-Di-p-methoxyphenyl cyclopropyl)-methyl]-γ-aminopropyl-3,4,5-trimethoxy benzoate hydrochloride (Formula VIIg)

Following the procedure of Example 16, 0.05 mole of 1-(N-γ-hydroxypropyl)-aminomethyl-2,2-di-p-methoxyphenyl cyclopropane hydrochloride, prepared in accordance with Example 13, are reacted with 0.055 mole of 3,4,5-trimethoxy benzoyl chloride. The hydrochloride is recrystallised from a mixture of ethanol and ether (70 : 30).

| Yield: | 79 % |
|---|---|
| Melting point: | 166 – 167°C |
| Analysis: | |
| Calculated | Found |
| N 2.45 % | N 2.33 % |

EXAMPLE 23

N-[(2,2-Di-p-fluorophenyl cyclopropyl)-methyl]-γ-aminopropyl-3,4,5-trimethoxy benzoate hydrochloride (Formula VIIh)

Following the procedure of Example 16, 0.05 mole of 1-(N-γ-hydroxypropyl)-aminomethyl-2,2-di-p-fluorophenyl cyclopropane hydrochloride, prepared in accordance with Example 14, are reacted with 0.055 mole of 3,4,5-trimethoxy benzoyl chloride. The hydrochloride is recrystallised from a mixture of ethanol and ether (80 : 20).

| Yield: | 58 % |
|---|---|
| Melting point: | 200 – 202°C |
| Analysis: | |
| Calculated | Found |
| N 2.56 % | N 2.63 % |

EXAMPLE 24

N-[(2,2-Di-p-chlorophenyl cyclopropyl)-methyl]-γ-aminopropyl-4-chlorobenzoate hydrochloride (Formula VIIi)

Following the procedure of Example 16, 0.05 mole of 1-(N-γ-hydroxypropyl)-aminomethyl-2,2-di-p-chlorophenyl cyclopropane hydrochloride, prepared in accordance with Example 15, are reacted with 0.055 mole of 4-chlorobenzoyl chloride. The hydrochloride is recrystallised from methanol.

| Yield: | 25 % |
|---|---|
| Melting point: | 208 – 210°C |
| Analysis: | |
| Calculated | Found |
| N 2.66 % | N 2.71 % |

The developed formulae of the products of Examples 16 to 24 are given in the following.

EXAMPLE 25

1-Aminomethyl-2,2-diphenyl cyclopropane hydrochloride (Formula IX R = H)

A 1000 cc capacity autoclave is charged with 0.5 mole of 1-cyano-2,2-diphenyl cyclopropane, 200 cc of ammoniacal methanol (100 g/l of NH$_3$) and 5 g of Raney nickel. In the presence of hydrogen, the reaction medium is stirred for 6 hours at 80°C/50 atms. pressure. After cooling, the reaction product is filtered, the nickel washed with 50 cc of methanol and the solvent evaporated in vacuo.

The evaporation residue is taken up in 300 cc of acetone, hydrogenchloride added up to pH 1, the mixture left standing for 2 hours, filtered, washed with 100 cc of acetone and dried.

| Yield: | 75 % |
|---|---|
| Melting point: | 251°C |
| Analysis: | |
| Calculated | Found |
| N 5.39 % | N 5.42 % |

EXAMPLE 26

1-Aminomethyl-2,2-di-p-tolyl cyclopropane hydrochloride (Formula IX R = 4-CH$_3$)

The title product is obtained in accordance with Example 25 using 0.5 mole of 1-cyano-2,2-di-p-tolyl cyclopropane instead of 0.5 mole of 1-cyano-2,2-diphenyl cyclopropane.

| Yield: | 71 % |
|---|---|
| Melting point: | 258°C |
| Analysis: | |
| Calculated | Found |
| N 4.86 % | N 4.70 % |

EXAMPLE 27

1-Aminomethyl-2,2-di-p-fluorophenyl cyclopropane hydrochloride (Formula IX R = 4-F)

The title product is obtained in accordance with Example 25 using 0.5 mole of 1-cyano-2,2-di-p-fluorophenyl cyclopropane instead of 0.5 mole of 1-cyano-2,2-diphenyl cyclopropane.

| Yield: | 71 % |
|---|---|
| Melting point: | 210°C |
| Analysis: | |
| Calculated | Found |
| N 4.74 % | N 4.72 % |

Examples 28 to 30 relate to the preparation by method B of the products of Examples 9, 12 and 14.

EXAMPLE 28

1-(N-γ-Hydroxypropyl)-aminomethyl-2,2-diphenyl cyclopropane hydrochloride (Formula V R = R$_1$ = H, A = CH$_2$CH$_2$CH$_2$)

A mixture of 0.5 mole of 1-aminomethyl-2,2-diphenyl cyclopropane, 0.52 mole of γ-cyclopropanol and 100 cc of xylene is heated with stirring to reflux temperature over a period of 7 hours.

The mixture is then allowed to return to ambient temperature and 400 cc of acetone added to it. The product is then stirred for 3 hours, filtered, washed with 100 cc of acetone and dried.

| Yield: | 50 % |
|---|---|
| Melting point: | 178°C |
| Analysis: | |
| Calculated | Found |
| N 4.42 % | N 4.38 % |

EXAMPLE 29

1-(N-γ-Hydroxypropyl)-aminomethyl-2,2-p-tolyl cyclopropane hydrochloride (Formula V R = 4-CH$_3$ R$_1$ = H A = (CH$_2$)$_3$)

The procedure is as in Example 28, except that 0.5 mole of 1-aminomethyl-2,2-di-p-tolyl cyclopropane are used instead of 0.5 mole of 1-aminomethyl-2,2-diphenyl cyclopropane.

| Yield: | 44 % |
|---|---|
| Melting point: | 195°C |
| Analysis: | |
| Calculated | Found |

-continued

| N 4.05 % | N 4.21 % |

EXAMPLE 30

1-(N-γ-Hydroxypropyl)-aminomethyl-2,2-di-p-fluorophenyl cyclopropane hydrochloride (Formula V R = 4-F $R_1$ = H A = $(CH_2)_3$)

The procedure is as in Example 28, except that 0.5 mole of 1-aminomethyl-2,2-di-p-fluorophenyl cyclopropane are used instead of 0.5 mole of 1-aminomethyl-2,2,-diphenyl cyclopropane.

| Yield: | 41 % |
|---|---|
| Melting point: | 148 – 150°C |
| Analysis: | |
| Calculated | Found |
| N 3.96 % | 4.07 % |

The results of pharmacological tests carried out with compounds of formula VII according to the invention are summarised in the following.

1. CORONARY VASODILATORY ACTIVITY ON ISOLATED HEARTS a. Method

Rabbits are killed and their hearts removed, being fixed by the aorta to a cannula in such a way that the end of the cannula is level with the orifice of the coronary arteries immediately above the sigmoid valvules. The hearts are perfused with oxygenated Ringer-Locke's solution kept at 37°C. An aqueous solution of the product to be tested is injected at the aortic cannula in a volume of 0.1 ml. The quantity of perfusion liquid is measured before and after administration of the product.

b. Results

Table I below shows the percentage increase in the coronary throughflow at the height of the phenomenon as a function of the quantity injected. Each result is the average result from five tests.

TABLE I

| Product of Example No. | Quantity injected | | | | |
|---|---|---|---|---|---|
| | 0.15 γ | 0.60 γ | 2.5 γ | 10 γ | 40 γ |
| 16 | 24 | 40 | 75 | 105 | — |
| 17 | — | — | 12 | 38 | 44 |
| 18 | 24 | 25 | 48 | 64 | |
| 19 | 17 | 31 | 55 | 61 | — |
| 20 | 23 | 42 | 75 | 93 | — |
| 21 | — | — | 21 | 27 | — |
| 22 | 11 | 30 | 58 | 70 | — |
| 23 | 12 | 37 | 60 | 62 | — |

2. ANTI-ARRHYTHMIC ACTIVITY a. Method

Rats weighing 180 to 200 g are anaesthetised by intraperitoneal injection of 1200 mg/kg of urethane. The jugular vein is perfused with a solution of aconitine hydrochloride (50 γ/ml) and sodium chloride (9 g/l) at a rate of 0.2 ml/min. The $D_2$-derivation electrocardiogram is recorded. Perfusion is stopped at the first ventricular arrhythmia. The products to be tested are administered by intravenous injection 1 minute before perfusion. The $D_2$-derivation electrocardiogram is an electrocardiogram recorded by fastening receptive electrodes to the right-hand front paw and to the left-hand rear paw, and an earth electrode to the right-hand rear paw.

b. Results

Table II below shows the percentage increases in the perfusion time as a function of the doses administered.

TABLE II

| mg/kg IV | Product of Example No. | | | | | | | | |
|---|---|---|---|---|---|---|---|---|---|
| | 16 | 17 | 18 | 19 | 20 | 21 | 22 | 23 | 24 |
| 1.25 | 41 | 30 | — | — | — | — | — | 23 | — |
| 2.50 | 53 | 72 | 22 | 4 | — | — | — | 57 | — |
| 5 | 86 | 94 | 51 | 71 | — | — | 16 | 87 | 5 |
| 10 | 122 | 135 | 79 | 109 | 33 | 25 | 46 | 145 | — |
| 20 | — | — | — | — | 44 | — | 112 | — | — |

3. PSYCHOTROPIC ACTIVITY

Studies were carried out on evasion, aggression and experimental cerebral anoxia.

EVASION a. Method

Mice (batches of eight per dose) are placed in groups of four in a cage with a sloping floor 30 minutes after interperitoneal administration of the products. The number of times they jump over a line marked on the sloping floor is counted over a period of 5 minutes. The percentage variation in relation to the controls is calculated.

b. Results

The results are set out in Table III below:

TABLE III

| Example | mg/kg I.P. | | | | | | |
|---|---|---|---|---|---|---|---|
| | 2 | 4 | 8 | 16 | 32 | 64 | 128 |
| 16 | — | — | +8 | −24 | −86 | −71 | — |
| 17 | −13 | — | −46 | — | −81 | — | — |
| 18 | — | −20 | — | −55 | — | −59 | — |
| 19 | — | — | −32 | — | −75 | — | −78 |
| 20 | — | — | — | −36 | — | −33 | — |
| 21 | +6 | — | −21 | — | −52 | — | — |
| 22 | — | −22 | −28 | −12 | — | — | — |
| 23 | — | — | −4 | −18 | −69 | — | — |

AGGRESSION THROUGH ISOLATION a. Method

Male Iffa mice weighing 16 to 17 g, which have been isolated for a period of 4 weeks are placed in pairs in the cage of one of them.

The number of "attacks" by one of the mice upon the other is counted every minute over a period of 5 minutes.

The substances to be tested are administered 30 minutes before the test to batches of 6 mice.

Table IV below shows the percentage decrease in the number of "attacks" over a period of 5 minutes.

b. Results

The results relating to the product of Example 16 are set out in Table IV.

TABLE IV

| mg/kg per os | Number of attacks in 5 minutes | % variation |
|---|---|---|
| 0 | 40 | — |
| 64 | 44 | +10 |
| 128 | 23 | −42 |
| 256 | 9 | −77 |
| 512 | 0 | −100 |

EXPERIMENTAL CEREBRAL ANOXIA IN RATS a. Method

Cortical electrodes are attached to the dura mater of rats. These electrodes are connected to a terminal fixed to the skull by a synthetic resin. The rats are tracheotomised under an ether anaesthetic, curarized by the intramuscular injection of 1 mg/kg of d-tubocuranine and placed under artificial respiration. The electroencephalogram (EEG) is recorded. The respiration pump is stopped every 3 minutes and switched on again 2 seconds after a flat EEG trace has been obtained.

The product, in the form of an aqueous solution, is perfused intravenously (285 γ/kg/min.). Perfusion begins 2 minutes after the first anoxia and lasts until the tenth anoxia. EEG Measurements are taken both on the period of time elapsing between stoppage of the pump and appearance of the flat trace and on the period of time elapsing between restarting of the pump and the appearance of a normal EEG trace. The ratio between these two periods is calculated.

The various measurements carried out with each anoxia are set out in Table V below.

b. Results

The results relating to the product of Example 16 are set out in Table V.

The products according to the invention, more particularly the products corresponding to general formula VII and their non-toxic acid addition salts, show experimentally coronarodilatory and anti-arrhythmic properties which enable them to be used as medicaments in cardiac disorders associated with inadequate irrigation and/or rhythmic troubles, their sedative and aggressolytic action promoting these properties. In addition, cerebral resistance to experimental anoxia is considerably increased which is indicative of favourable activity in syndromes associated with a deficiency of cerebral cellular respiration.

In clinics, favourable results were obtained in the treatment of cardiac disorders by administering the compounds of formula II and their non-toxic acid addition salts in the form of tablets, dragees or capsules containing 50 to 100 mg of active principle, suppositories containing 100 mg or more of active principle, suspensions for oral administration containing from 5 to 10 mg/ml of active principle, in a daily dose of on average between 50 and 400 mg. It was possible to administer the products of Example 16 in a daily dose of up to 500 mg without observing any side effects.

The clinical tests carried out with the product of Example 16 are summarised in the following. This product, administered to patients suffering from crises of chest angina, enabled the doses of trinitrine normally taken to be reduced.

In old people living in a home for the aged, the product of Example 16 enabled the subjects treated to perform better in tests demonstrating a level of co-ordination and association of ideas better than those measured before treatment.

In these tests, the product of Example 16 was used in the form of capsules containing 100 mg of active principle or in the form of a drinkable suspension containing 5 mg/ml of active principle, the average daily doses varying from 100 to 300 mg.

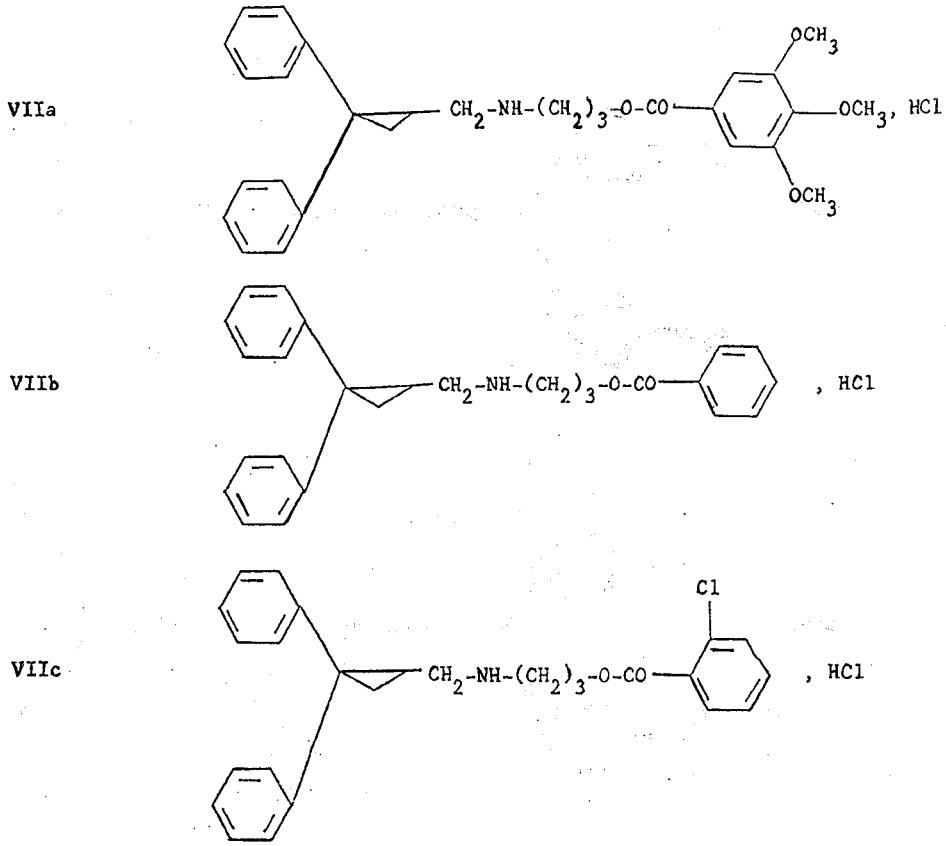

VIId 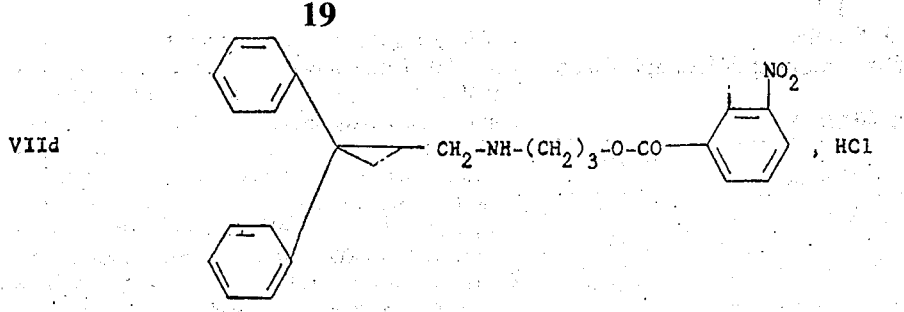
VIIe 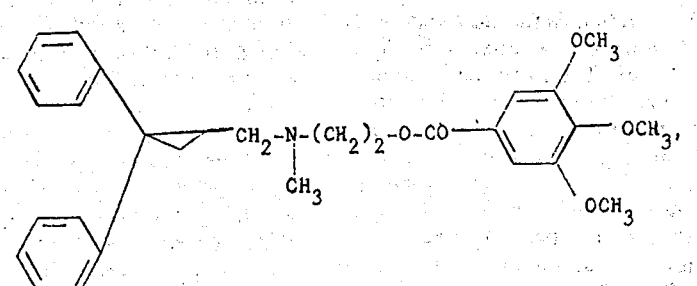
VIIf 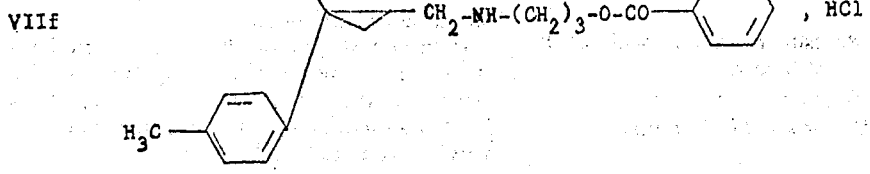
VIIg 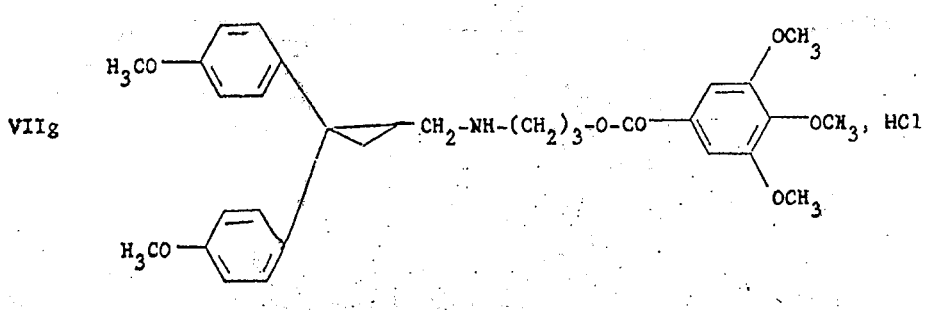
VIIh 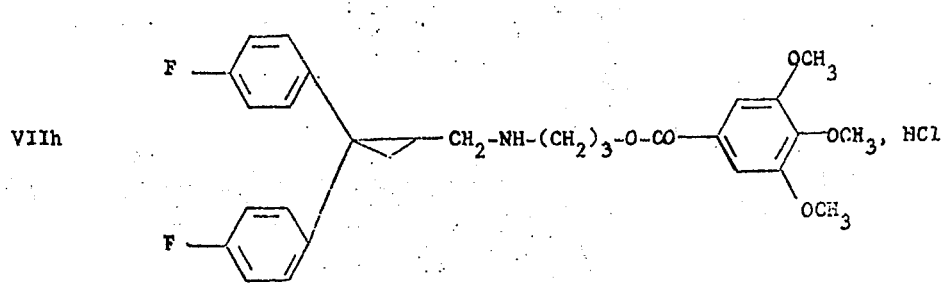

VIIi 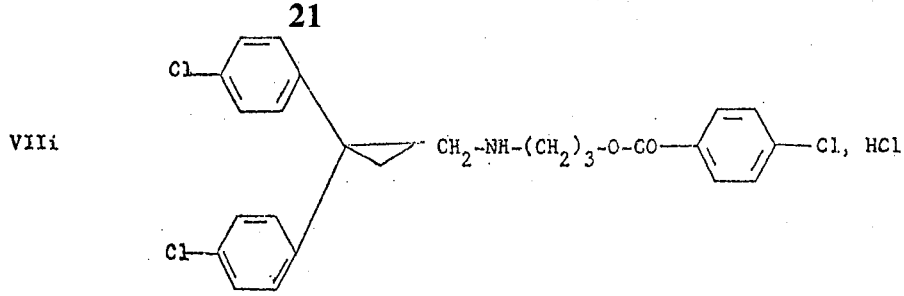

TABLE V

| Anoxia No. | | 1 | 2 | 3 | 4 | 5 | 6 | 7 | 8 | 9 | 10 |
|---|---|---|---|---|---|---|---|---|---|---|---|
| Resistance to anoxia in seconds | Controls | 48,5 ± 4,55 | 45,6 ± 3,61 | 45,3 ± 3,07 | 46,7 ± 2,42 | 47,3 ± 2,59 | 46,4 ± 2,47 | 45,6 ± 2,49 | 45,6 ± 2,59 | 46,0 ± 2,47 | 46,1 ± 2,62 |
| | Example 16 | 53,1 ± 3,48 | 50,7 ± 2,31 | 51,6 ± 1,90 | 53,9 ± 2,32 | 54,4 ± 2,58 | 56,2 ± 2,72 | 56,6 ± 2,80 | 57,9 ± 2,59 | 58,5 ± 2,85 | 58,5 ± 2,99 |
| Flat trace in seconds | Controls | 10,4 ± 0,57 | 11,3 ± 0,68 | 12,4 ± 0,74 | 14,6 ± 1,21 | 16,5 ± 1,17 | 18,3 ± 1,25 | 20,4 ± 1,42 | 22,8 ± 1,57 | 25,2 ± 2,19 | 29,6 ± 9,54 |
| | Example 16 | 10,7 ± 0,57 | 11,8 ± 1,41 | 12,1 ± 0,72 | 12,7 ± 0,68 | 12,5 ± 0,74 | 12,6 ± 0,78 | 12,0 ± 0,60 | 13,0 ± 0,68 | 12,8 ± 0,78 | 12,3 ± 0,84 |
| Ratio: Resistance to anoxia | Controls | 4,8 ± 0,43 | 4,3 ± 0,50 | 3,9 ± 0,41 | 3,5 ± 0,40 | 3,1 ± 0,28 | 2,7 ± 0,31 | 2,4 ± 0,28 | 2,1 ± 0,24 | 2,0 ± 0,30 | 1,7 ± 0,22 |
| Flat trace | Example 16 | 5,2 ± 0,43 | 4,6 ± 0,37 | 4,3 ± 0,36 | 4,4 ± 0,37 | 4,4 ± 0,40 | 4,8 ± 0,62 | 4,7 ± 0,33 | 4,5 ± 0,28 | 4,7 ± 0,40 | 4,9 ± 0,41 |

We claim:
1. 2,2-diarylcyclopropane derivatives selected from the group consisting of:
a. the compounds corresponding to the formula:

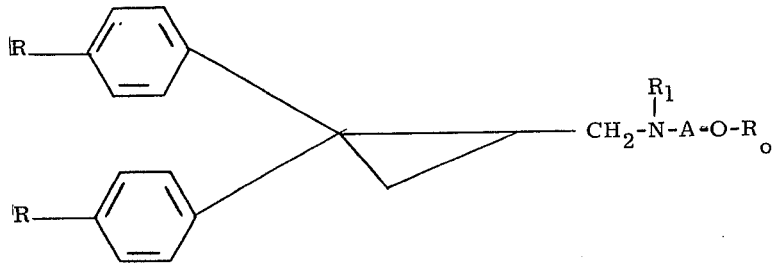

in which R represents H, Cl, F, $CH_3$, $OCH_3$; A represents $C_1$–$C_5$ alkylene group, $R_1$ represents H, $CH_3$; $R_0$ is a benzoyl group of the formula

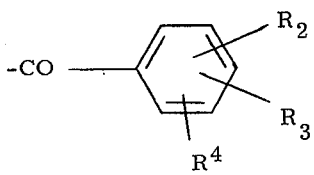

in which $R_2$, $R_3$ and $R_4$, which may be the same or different, each represent H, Cl, $NO_2$, $CH_3$, $OCH_3$.

2. N-(2,2-Diphenylcyclopropylmethyl)-γ-aminopropyl-3,4,5-trimethoxy benzoate and its acid addition salts.

3. N-(2,2-Diphenylcyclopropylmethyl)-μ-aminopropyl benzoate and its acid addition salts.

4. N-(2,2-Diphenylcyclopropylmethyl)-γ-aminopropyl-2-chlorobenzoate and its acid addition salts.

5. N-(2,2-Diphenylcyclopropylmethyl)-γ-aminopropyl-3-nitrobenzoate and its acid addition salts.

6. N-Methyl-N-[(2,2-diphenylcyclopropyl)-methyl]-β-aminoethyl-3,4,5-trimethoxybenzoate and its acid addition salts.

7. N-[(2,2-Di-p-tolylcyclopropyl)-methyl]-γ-aminopropyl-2-methyl benzoate and its acid addition salts.

8. N-[(2,2-Di-p-methoxyphenylcyclopropyl)-methyl]-γ-aminopropyl-3,4,5-trimethoxybenzoate and its acid addition salts.

9. N-[(2,2-Di-p-fluorophenylcyclopropyl)-methyl]-γ-aminopropyl-3,4,5-trimethoxybenzoate and its acid addition salts.

* * * * *